(12) United States Patent
Silcott

(10) Patent No.: US 9,851,291 B2
(45) Date of Patent: Dec. 26, 2017

(54) REALTIME OPTICAL METHOD AND SYSTEM FOR DETECTING AND CLASSIFYING BIOLOGICAL AND NON-BIOLOGICAL PARTICLES

(71) Applicant: HAMILTON ASSOCIATES, INC., Owing Mills, MD (US)

(72) Inventor: David B. Silcott, Reisterstown, MD (US)

(73) Assignee: HAMILTON ASSOCIATES, INC., Owings Mills, MD (US)

( * ) Notice: Subject to any disclaimer, the term of this patent is extended or adjusted under 35 U.S.C. 154(b) by 0 days.

(21) Appl. No.: 15/143,726

(22) Filed: May 2, 2016

(65) Prior Publication Data
US 2017/0315045 A1 Nov. 2, 2017

(51) Int. Cl.
| | |
|---|---|
| *G01N 21/00* | (2006.01) |
| *G01J 4/00* | (2006.01) |
| *G01N 15/14* | (2006.01) |
| *G01N 15/02* | (2006.01) |
| *G01N 15/00* | (2006.01) |

(52) U.S. Cl.
CPC ..... *G01N 15/1434* (2013.01); *G01N 15/0211* (2013.01); *G01N 15/1429* (2013.01); *G01N 2015/0065* (2013.01)

(58) Field of Classification Search
CPC .................................. G01N 21/00; G01J 4/00
USPC ................................................... 356/337, 364
See application file for complete search history.

(56) References Cited

U.S. PATENT DOCUMENTS

| | | | |
|---|---|---|---|
| 3,600,094 | A | 8/1971 | Liskowitz |
| 3,612,688 | A | 10/1971 | Liskowitz |
| 3,721,500 | A | 3/1973 | Fugitt |
| 3,817,634 | A | 6/1974 | Barron et al. |
| 4,796,995 | A | 1/1989 | Salzman et al. |
| 4,884,886 | A | 12/1989 | Salzman et al. |

(Continued)

FOREIGN PATENT DOCUMENTS

| | | |
|---|---|---|
| CN | 200963473 U | 10/2007 |
| CN | 100360957 C | 1/2008 |

(Continued)

OTHER PUBLICATIONS

"Advanced Trigger Development," by Thomas H. Jeys et al, Lincoln Laboratory Journal, 17(1) p. 29-62 (2007)(NPL 1).

(Continued)

*Primary Examiner* — Roy M Punnoose
(74) *Attorney, Agent, or Firm* — Merek, Blackmon & Voorhees, LLC

(57) ABSTRACT

Methods, apparatuses, and systems for detecting and classifying individual airborne biological and non-biological particles, in real time, based on particle size and polarized elastic scatter. Auto-fluorescence content may also be used along with particle size and polarized elastic scatter for further orthogonal classification. With polarized elastic scattering, the degree of linear or circular depolarization produced from particle morphology, refractive index, internal asymmetric structures and molecular optical activity can be used for classifying individual airborne particles. Alternatively, circular intensity differential scattering (CIDS) or linear intensity differential scattering (LIDS) can be used to discriminate individual particles.

25 Claims, 14 Drawing Sheets

(56) References Cited

U.S. PATENT DOCUMENTS

Figure 1:
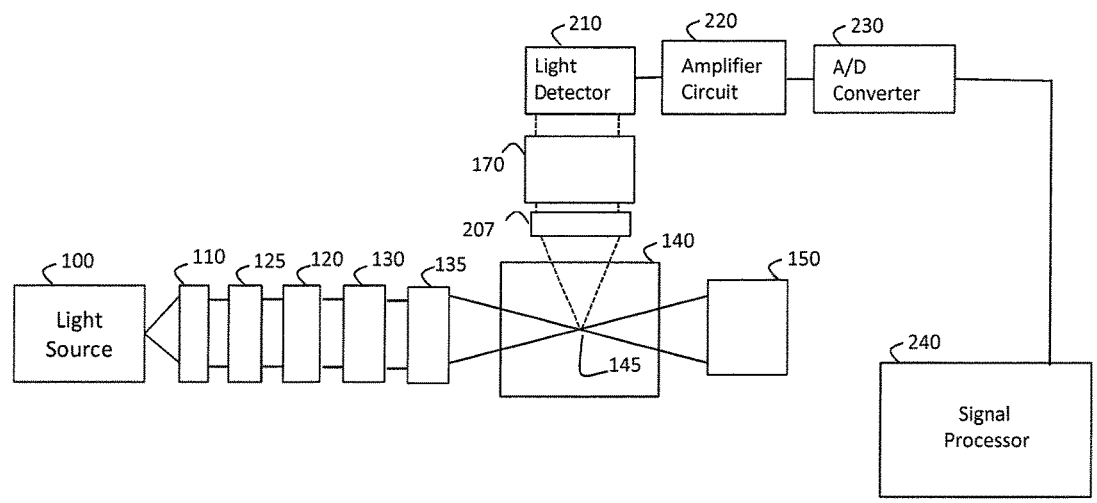

| | | | |
|---|---|---|---|
| 5,017,497 | A | 5/1991 | Gerard de Grooth et al. |
| 5,046,847 | A | 9/1991 | Nakata et al. |
| 5,254,861 | A | 10/1993 | Carpenter et al. |
| 5,543,018 | A | 8/1996 | Stevens et al. |
| 5,701,012 | A | 12/1997 | Ho |
| 5,895,922 | A | 4/1999 | Ho |
| 5,999,250 | A | 12/1999 | Hairston et al. |
| 6,060,710 | A | 5/2000 | Carrieri et al. |
| 6,118,536 | A | 9/2000 | Sakamoto et al. |
| 6,194,731 | B1 | 2/2001 | Jeys et al. |
| 6,421,121 | B1 | 7/2002 | Haavig et al. |
| 6,441,387 | B1 | 8/2002 | DeSha |
| 6,448,923 | B1 | 9/2002 | Zrnic et al. |
| 6,532,067 | B1 | 3/2003 | Chang et al. |
| 6,639,674 | B2 | 10/2003 | Sokolov et al. |
| 6,694,799 | B2 | 2/2004 | Small |
| 6,831,279 | B2 | 12/2004 | Ho |
| 6,885,440 | B2 | 4/2005 | Silcott et al. |
| 6,967,338 | B1 | 11/2005 | Sickenberger et al. |
| 7,053,783 | B2 | 5/2006 | Hamburger et al. |
| 7,057,712 | B2 | 6/2006 | Beck |
| 7,106,442 | B2 * | 9/2006 | Silcott ............... G01N 15/1459 356/336 |
| 7,260,483 | B2 | 8/2007 | Gard et al. |
| 7,304,742 | B1 | 12/2007 | Gurton |
| 7,333,190 | B1 | 2/2008 | Pendell-Jones et al. |
| 7,339,670 | B2 | 3/2008 | Carrig et al. |
| 7,359,040 | B1 | 4/2008 | Pendell-Jones et al. |
| 7,375,348 | B1 | 5/2008 | Sickenberger et al. |
| 7,423,751 | B2 | 9/2008 | Hairston et al. |
| 7,430,046 | B2 | 9/2008 | Jiang et al. |
| 7,525,660 | B2 | 4/2009 | Gigioli et al. |
| 7,554,663 | B2 | 6/2009 | Hairston et al. |
| 7,576,844 | B2 | 8/2009 | Hairston et al. |
| 7,580,127 | B1 | 8/2009 | Mayor et al. |
| 7,800,755 | B1 | 9/2010 | Poirier et al. |
| 7,852,469 | B1 | 12/2010 | Sickenberger et al. |
| 7,920,261 | B2 | 4/2011 | Jeys et al. |
| 7,981,365 | B2 | 7/2011 | Hart et al. |
| 7,986,408 | B2 | 7/2011 | Ray et al. |
| 8,031,339 | B2 | 10/2011 | Steele |
| 8,078,410 | B2 | 12/2011 | Marquardt et al. |
| 8,098,428 | B2 | 1/2012 | Kawai et al. |
| 8,213,010 | B2 | 7/2012 | Sivaprakasam |
| 8,218,144 | B2 | 7/2012 | Jiang et al. |
| 8,274,655 | B2 | 9/2012 | Herzog |
| 8,520,205 | B2 | 8/2013 | Silcott |
| 8,540,946 | B2 | 9/2013 | Padmanabhan et al. |
| 8,628,976 | B2 | 1/2014 | Bolotin et al. |
| 8,797,533 | B2 | 8/2014 | Sunami et al. |
| 2005/0243307 | A1 * | 11/2005 | Silcott ............... G01N 15/1459 356/73 |
| 2006/0238757 | A1 | 10/2006 | Silcott |
| 2008/0139914 | A1 | 6/2008 | Gaved et al. |
| 2010/0137163 | A1 | 6/2010 | Link et al. |
| 2011/0058167 | A1 | 3/2011 | Knox et al. |
| 2012/0105849 | A1 | 5/2012 | Sivaprakasam |
| 2015/0276481 | A1 | 10/2015 | Liu et al. |

FOREIGN PATENT DOCUMENTS

| | | |
|---|---|---|
| CN | 100511304 C | 7/2009 |
| CN | 202067058 U | 12/2011 |
| CN | 104089855 | 10/2014 |
| DE | 1003570 | 2/2002 |
| JP | 2004279143 | 10/2004 |
| JP | 3940235 | 7/2007 |
| JP | 4713531 | 6/2011 |
| KR | 20150086652 | 7/2015 |
| WO | WO 2007/131038 | 11/2007 |
| WO | WO2015/160418 | 10/2015 |

OTHER PUBLICATIONS

"Optical Techniques for Detecting and Identifying Biological-Warfare Agents," by Darryl P. Greenwood et al, Lincoln Laboratory Journal, 97(6), p. 971-989 (2009)(NPL 2).

"Circular differentially scattering can be an important part of the circular dichroism of macromolecules," by Carlos Bustamante et al, PNAS, vol. 80, pp. 3568-3572 (1983)(NPL 3).

"Rapid identification of microorganisms by circular-intensity differential scattering," Gary Salzman et al, Applied and Environmental Microbiology, vol. 44(5), pp. 1081-1085 (1982)(NPL 4).

"Application of polarization effects in light scattering: A new biophysical tool," PNAS, vol. 73(2), pp. 486-490 (1976)(NPL 5).

"Circular intensity differential scattering of light by helical structures. I. Theory," The Journal of Chemical Physics, vol. 73, pp. 4273-4281 (1980)(NPL 6).

"Circular intensity differential scattering of light by helical structures. II. Applications," Carlos Bustamante et al, The Journal of Chemical Physics, vol. 73, pp. 6046-6055 (1980)(NPL 7).

"Circular intensity differential scattering of light by helical structures. III. A general polarizability tensor and anomalous scattering," Carlos Bustamante et al, The Journal of Chemical Physics, vol. 74, pp. 4839-4850 (1981)(NPL 8).

Machine translation of CN100360957C the accuracy of which is not known nor conceded to by Applicant.

Machine translation of CN100511304C the accuracy of which is not known nor conceded to by Applicant.

Machine translation of CN104089855 the accuracy of which is not known nor conceded to by Applicant.

Machine translation of CN200963473U the accuracy of which is not known nor conceded to by Applicant.

Machine translation of CN202067058U the accuracy of which is not known nor conceded to by Applicant.

Machine translation of DE10035709 the accuracy of which is not known nor conceded to by Applicant.

Machine translation of JP2004279143 the accuracy of which is not known nor conceded to by Applicant.

Machine translation of JP3940235 the accuracy of which is not known nor conceded to by Applicant.

Machine translation of JP4713531 the accuracy of which is not known nor conceded to by Applicant.

Machine translation of KR20150086652 the accuracy of which is not known nor conceded to by Applicant.

"Single ice crystal measurements during nucleation experiments with the depolarization detector IODE", Atmos. Chem. Phys., 10, pp. 313-325, 2010 (NPL 9).

"Circular depolarization ratios of single water droplets and finite ice circular cylinders: a modeling study", Atmos. Chem. Phys., 12, pp. 4207-4214, 2012 (NPL 10).

"Development of a Bioaerosol single particle detector (Bio In) for the Fast Ice Nucleus CHamber FINCH", Atmos. Meas. Tech., 3, pp. 263-271, 2010 (NPL 11).

"Comparison of various linear depolarization parameters measured by lidar", Applied Optics vol. 38, Issue 21, Abstract, 1999 (NPL 12).

"Depolarization of backscattered linearly polarized light", vol. 21, No. 9/Sep. 2004/J. Opt. Soc. Am. A pp. 1799-1804 (NPL 13).

"Polarization in Lidar", Kenneth Sassen, Geophysical Institute, University of Alaska Fairbanks, Fairbanks, Alaska, U.S.A. (ksassen@gi.alaska.edu), pp. 19 to 42 (NPL 14).

International Search Report issued in connection with PCT/US 17/26933, 2 pages (NPL1).

Written Opinion of the International Searching Authority issued in connection with PCT/US 17/26933, 7 pages (NPL2).

* cited by examiner 3 micron diameter Bacillus globigii spore aggregate a – represents scatter signal from horizontally polarized excitation
b – represents scatter signal from vertically polarized excitation

Figure 9

|  | Number Particle Size | Surface Particle Size | Mass Particle Size |
| --- | --- | --- | --- |
| Median ($\mu$m) | 0.819 | 0.855 | 0.873 |
| Mean ($\mu$m) | 0.811 | 0.864 | 0.892 |
| Geo. Mean ($\mu$m) | 0.797 | 0.850 | 0.878 |
| Mode ($\mu$m) | 0.835 | 0.835 | 0.898 |
| Geo. St. Dev. | 1.20 | 1.19 | 1.20 |
| Total Conc. | 0.264(#/cm$^3$) | 0.563($\mu$m$^2$/cm$^3$) | 8.10e-05(mg/m$^3$) |

Figure 13

REALTIME OPTICAL METHOD AND SYSTEM FOR DETECTING AND CLASSIFYING BIOLOGICAL AND NON-BIOLOGICAL PARTICLES

FIELD OF INVENTION

This invention pertains generally to aerosol analyzers and more specifically to optical analyzers for the real-time detection and classification of airborne biological and non-biological particles.

BACKGROUND OF INVENTION

There has been significant progress over the last 15 years in the development of both methods and systems that provide real-time detection and classification of airborne biological and non-biological particles. Most of the methods and systems have been based on optical approaches that utilize both particle sizing and laser induced fluorescence (LIF) to discriminate biological from non-biological particles. These methods have included illumination approaches using various wavelengths specific towards exciting endogenous fluorophores commonly found in biological particles. LIF based approaches have also included multiple excitation sources operating at different wavelengths for improved classification. Other approaches have included laser breakdown spectroscopy coupled with LIF detection for measuring both auto-fluorescence and mineral content of single particles, as well as, Raman spectroscopy and Fourier transform infrared spectroscopy of single particles.

There is a growing need for improved environmental biosurveillance in such areas as battlefield and homeland defense, indoor and outdoor air quality monitoring, airborne hospital infection control, contamination control monitoring of biopharmaceutical and other manufacturing operations, sewage plants, animal production houses and other operations where continuous real-time monitoring helps provide early warning and prevention of harmful exposure of microorganisms, viruses and other types of biological particles. With respect to defense applications, the deadliest form of a biological attack is from aerosolized agents. To date, optical methods that utilize both particle sizing and laser induced fluorescence have been applied to battlefield and homeland defense. This approach has proven to be an effective early warning capability, in particular, for building protection applications that monitor for indoor biological attacks. To a lesser extent, real-time airborne microbial monitoring using LIF based detection has been applied towards contamination control monitoring of biopharmaceutical manufacturing and other clean room operations. While these LIF based biological particle counter methods have shown to be useful early warning systems, they are not without limitations and significant room for improvement exists.

There are three primary limitations with LIF based biological particulate detection. First, is their ability to detect single vegetative or spore type organisms. Current fielded LIF based biological particle detectors are limited to detection of vegetative cell and spore aggregate particles or particles that contain numerous vegetative cells or spores per aerosol particle. For both biodefense and other applications the detection of single vegetative cells and spores is required and necessary to provide adequate protection or effective contamination control monitoring. For LIF based approaches, unless a laser source with considerable optical power is used an insufficient amount of light is emitted from fluorescence excitation to reliably and accurately classify a biological from a non-biological particle when the particle size is in the 0.5-1.5 micron diameter in size. This is particularly true for longer excitation wavelengths such as the 350-450 nm wavelength range but also applies, in most instances, for shorter wavelengths such as the 250-300 nm wavelength range.

Second, their ability to discriminate biological from non-biological particles and to classify biological particle types, such as bacterial spores, mold spores, vegetative bacteria, viral aggregates, protein toxin aggregates, and fomite particles containing bacteria, viruses, or fungi is very limited. With a minimum need for discrimination of biological from non-biological, the use of LIF based particle detection approaches are useful for discrimination from inorganic particles and non-fluorescing man-made particles but face serious limitations for particles that have been doped with fluorophores, such as paper particles or clothing particles containing optical brighteners, and commonly encountered particles that have intrinsic fluorescence, such as human skin cell fragments and animal dander. The use of LIF based multi-wavelength excitation approaches have some improved classification over single source approaches but the approaches are not cost effective for widespread application.

Third, current LIF based approaches are limited in their ability to detect biological particle concentration levels of interest, particularly in applications where detection of only a fraction to a few particles per liter of air is required. The ability to both detect in a timely manner and to discriminate these low levels from commonly encountered aerosol backgrounds becomes very challenging for LIF based biological particle detection approaches. Current systems are limited to 1-3 liter per minute air sampling flow rates. This equates to slow response times and long sampling times in order to detect and alarm on the presence of a low concentration of biological particles. The use of aerosol concentrators to compensate for this are limited in their application because the problem of discrimination increases with the increase in sampling flow rate and background aerosol concentration.

SUMMARY OF THE INVENTION

Preferred embodiments of the present invention contemplate methods, apparatuses, and systems for detecting and classifying individual airborne biological and non-biological particles, in real time, based on polarized elastic scatter. Particle size and/or autofluorescene content may also be used along with polarized elastic scatter for further orthogonal classification. With polarized elastic scattering, the degree of linear or circular depolarization produced from particle morphology, refractive index, internal asymmetric structures and molecular optical activity can be used for classifying individual airborne particles. Additionally, circular intensity differential scattering (CIDS) and linear intensity differential scattering (LIDS) provide a means for discriminating individual particles. CIDS is based mainly on a particle's intrinsic molecular optical activity and internal asymmetric structures, such as from chiral macromolecular complexes and aggregates commonly found in biological particles. LIDS is based on a particle's shape or morphology, refractive index, intrinsic optical activity and internal asymmetric structures.

When linear depolarization detection is used, the normalized depolarization of light scattered from a particle can be determined by the relationship:

$$\delta_N = [I_V]/[I_H + I_V]$$

Where $\delta_N$ represents normalized depolarization, $I_H$ represents the scatter intensity for horizontally polarized light and is the same as the as the polarization state of the illumination beam and $I_V$ represents the scatter intensity for vertically polarized light. In another configuration, two incident beams of orthogonal linear polarizations can be used for illumination of individual particles and scattered horizontally polarized light is used for measuring the degree of depolarization. In this configuration the ratio of scattered intensity of horizontally polarized light collected during two spatially separated orthogonally linear polarized incident beams can be used to classify individual particles and is given by the relationship:

$$\delta = I_{HV}/I_{HH}$$

Where $\delta$ represents depolarization, $I_{HH}$ represents the scatter intensity for horizontally polarized light and horizontally polarized incident beam, $I_{HV}$ represents the scatter intensity for horizontally polarized light and a vertically polarized incident beam.

When circular depolarization detection is used, the normalized depolarization of light scattered from a particle can be determined by the relationship:

$$\delta_{+C} = [I_\perp]/[I_\| + I_\perp]$$

$$\delta_{-C} = [I_\|]/[I_\| + I_\perp]$$

Where $\delta_{+C}$ represents circular depolarization when using right handed polarized light as the illumination source, $\delta_{-C}$ represents circular depolarization when using left handed polarized light as the illumination source, $I_\perp$ represents the scatter intensity for perpendicularly polarized light and $I_\|$ represents the scatter intensity for parallel polarized light. With this approach either a single circularly polarized source can be used for illumination or two incident beams of right and left handed circular polarization can be used for illumination of individual particles and scattered perpendicularly and parallel polarized light is used for measuring the degree of depolarization. In the dual beam configuration, the ratio of scattered intensity of perpendicularly and parallel polarized light collected during two spatially separated left and right handed circular polarized incident beams can be used to classify individual particles.

When CIDS detection is used, differential scattering of left and right circularly polarized light contributes to the circular dichroism of biological macromolecules. When the diameter of the particle or macromolecular complex exceeds $\frac{1}{20}^{th}$ the excitation wavelength the differential scattering contribution to circular dichroism becomes important. When using an excitation wavelength outside the absorption band of the chiral particle only differential scattering contributes to the circular dichroism. A chiral scattering particle will produce a differential scattering signal where both its sign and magnitude are directly related to the relative orientations and distances between its chiral scattering elements. This signal can be obtained in a quantitative manner and can be used for discrimination of biological from non-biological particles and for classifying one biological type particle from another. As an example, for a helical structure such as a DNA molecule or an alpha-helix strand in a protein the differential scattering of left and right circularly polarized light is sensitive to the pitch and radius of the helix, as well as, the wavelength of the excitation source. The circular intensity differential scattering (CIDS) at a scattering angle $\theta$ can be determined by the relationship:

$$[I_L(\theta) - I_R(\theta)]/[I_L(\theta) + I_R(\theta)],$$

Where $I_L(\theta)$ is the light scattered at angle $\theta$ when the incident beam is left circularly polarized and $I_R(\theta)$ is the light scattered at angle $\theta$ when the incident beam is right circularly polarized. CIDS is not sensitive to size, shape or refractive index but is sensitive to the chirality of biological macromolecules which are present in all airborne bacteria, fungi, viruses and protein aggregate particles.

When LIDS detection is used, differential scattering of vertically and horizontally polarized light is sensitive to the shape, refractive index and chiral content of particles, or more specifically, internal asymmetric structures and molecular optical activity. The linear intensity differential scattering (LIDS) at a scattering angle θ can be determined by the relationship:

$$[I_H(\theta) - I_V(\theta)]/[I_H(\theta) + I_V(\theta)],$$

Where $I_H(\theta)$ is the light scattered at angle θ when the incident beam is horizontally polarized and $I_V(\theta)$ is the light scattered at angle θ when the incident beam is vertically polarized. LIDS is sensitive to size, shape and refractive index and is also sensitive to the chirality of biological macromolecules which are present in all airborne bacteria, fungi, viruses and protein aggregate particles.

When linear depolarization detection is used, one preferred embodiment of the present invention includes a method for detecting and classifying a single particle comprising illuminating the particle with a linearly polarized light beam where its polarization is alternated from horizontal to vertical with two vertically spaced beams produced from a single source as the particle traverses the illumination region. A single detector employing a horizontally polarized filter thereby captures polarized and depolarized scattering signals on single particles. The size of the particle can be determined by measuring the elastic scatter intensity with the horizontally polarized source. The degree of depolarization for a certain particle size range may then be compared to a library of signatures for various biological and non-biological type aerosols. With this method an orthogonal fluorescence detection channel can be added provided the selection of the source's excitation is one that can excite the desired endogenous fluorophores commonly encountered in biological particles.

When circular depolarization detection is used, one preferred embodiment of the present invention includes a method for detecting and classifying a single particle comprising illuminating the particle with a circularly polarized light beam where its polarization is alternated from right handed to left handed with two vertically spaced beams produced from a single source as the particle traverses the illumination region. A polarizing beam splitter with two detectors captures parallel and perpendicularly polarized scattering signals on single particles. The size of the particle can be determined by summing the intensity of the two polarized scatter signals. The degree of depolarization for a certain particle size range may then be compared to a library of signatures for various biological and non-biological type aerosols. With this method, an orthogonal fluorescence detection channel can be added provided the selection of the source's excitation is one that can excite the desired endogenous fluorophores commonly encountered in biological particles.

When CIDS detection is used, one preferred embodiment of the present invention includes a method for detecting and classifying a single particle comprising illuminating the particle with a circularly polarized light beam where its polarization is alternated from left to right (or right to left) handedness with two vertically spaced beams produced from a single source as the particle traverses the illumination region thereby capturing circular intensity differential scattering signals on single particles. The size of the particle can be determined by measuring the elastic scatter intensity. The intensity of left handed and right handed circular scatter signals is used to determine the CIDS value per aerosol event. The CIDS value may then be compared to a library of signatures for various biological and non-biological type aerosols. Also with this method an orthogonal fluorescence detection channel can be added provided the selection of the source's excitation is one that can excite the desired endogenous fluorophores commonly encountered in biological particles.

When LIDS detection is used, one preferred embodiment of the present invention includes a method for detecting and classifying a single particle comprising illuminating the particle with a linearly polarized light beam where its polarization is alternated from horizontal to vertical with two vertically spaced beams produced from a single source as the particle traverses the illumination region thereby capturing linear intensity differential scattering signals on single particles. The size of the particle can be determined by measuring the elastic scatter intensity. The intensity of vertically and horizontally polarized scatter signals is used to determine the LIDS value per aerosol event. The LIDS value may then be compared to a library of signatures for various biological and non-biological type aerosols. Also, with this method, an orthogonal fluorescence detection channel can be added provided the selection of the source's excitation is one that can excite the desired endogenous fluorophores commonly encountered in biological particles.

The above summary describes preferred forms of the present invention and is not in any way to be construed as limiting the claimed invention to the preferred forms.

BRIEF DESCRIPTION OF THE DRAWINGS

FIG. 1 is a schematic representation illustrating an optical detector including a linear depolarization detection configuration having a dual vertically and horizontally polarized beam source and a single detector with horizontally polarized filter.

FIG. 1A is an enlarged schematic representation illustrating a preferred optical viewing region having two illumination points or areas.

FIG. 2 is a schematic representation illustrating an optical detector including a linear depolarization detection configuration having a single horizontally polarized beam source and two detectors with one having a horizontally polarized filter and the other a vertically polarized filter.

FIG. 3 is a schematic representation illustrating an optical detector including a linear depolarization detection configuration having a dual vertically and horizontally polarized beam source and a single detector with horizontally polarized filter and an orthogonal fluorescence detection channel.

FIG. 4 is a schematic representation illustrating an optical detector including a linear depolarization detection configuration having a vertically and horizontally polarized beam source, a polarizing beam splitter and two detectors for detecting parallel and perpendicularly polarized scatter.

FIG. 5 is a schematic representation illustrating an optical detector including a circular depolarization detection configuration having a dual left handed and right handed circularly polarized beam source, a polarizing beam splitter and two detectors for detecting parallel and perpendicularly polarized scatter.

FIG. 6 is a schematic representation illustrating an optical detector including a circular intensity differential scattering detection configuration having a dual left handed and right handed circularly polarized beam source and a single detector.

FIG. 7 is a schematic representation illustrating an optical detector including a linear intensity differential scattering detection configuration having a dual vertically and horizontally polarized beam source and a single detector.

FIG. 8 is a schematic representation illustrating an optical detector including a linear depolarization detection configuration having a single horizontally polarized beam source and a single detector having a vertically polarized filter and an orthogonal fluorescence detection channel.

FIG. 9 illustrates the detection event for a single particle for the optical analyzer depicted in FIG. 1.

FIGS. 10 and 11 illustrate the linear depolarization response where the degree of depolarization is determined by dividing the scatter intensity collected from a horizontally polarized filtered signal and a horizontally polarized excitation source by the scatter intensity collected from a horizontally polarized filtered signal and a vertically polarized excitation source.

FIG. 12 illustrates additional linear depolarization responses using the same ratio measurement as in FIGS. 10 and 11 and the use of depolarization ratio distributions to classify particles of interest from commonly encountered particles from different environments. Three different environments are provided as examples: an indoor building, a subway platform and an urban background.

FIG. 13 illustrates additional linear depolarization responses using the same ratio measurement as in FIGS. 10 and 11 and 3D scatter analysis approach.

DETAILED DESCRIPTION OF THE PREFERRED EMBODIMENTS OF THE INVENTION

The preferred forms of the presented invention will now be described with reference to FIGS. 1-13. The appended claims are not limited to the preferred forms and no term and/or phrase used herein is to be given a meaning other than its ordinary meaning unless it is expressly stated otherwise. The use of like reference numerals indicate the same component and/or feature except when otherwise indicated.

The preferred forms of the present invention relate to enhanced methods, apparatuses and systems for the detection and classification of biological and non-biological particulates in a real-time manner. The various detection schemes exploit one physical phenomena which involves the interaction of light with a single aerosol particle (i.e., polarized elastic scattering). A second physical phenomena which involves the interaction of light with a single aerosol particle may be used (i.e., fluorescence). In addition to these optical phenomena (i.e., polarized elastic scattering and fluorescence), the particle's size is preferably determined substantially simultaneously.

The preferred forms of the present invention are capable of detecting and classifying single airborne particles having an aerodynamic diameter of 10 microns or less (e.g., 0.5 to 1.5 microns).

Described herein are eight optical detectors having aerosol sensing configurations which are variations of linearly polarized and circularly polarized excitation approaches. Particle sizing using polarized elastic scatter detection is applicable to all the sensing configurations with the exception of FIG. 8. In all configurations aerosol is drawn preferably by a vacuum source (not shown) into an optical viewing region at 0.01 to 100 liters per minute and particles are illuminated one at a time with one or more light beams.

Figure 5:
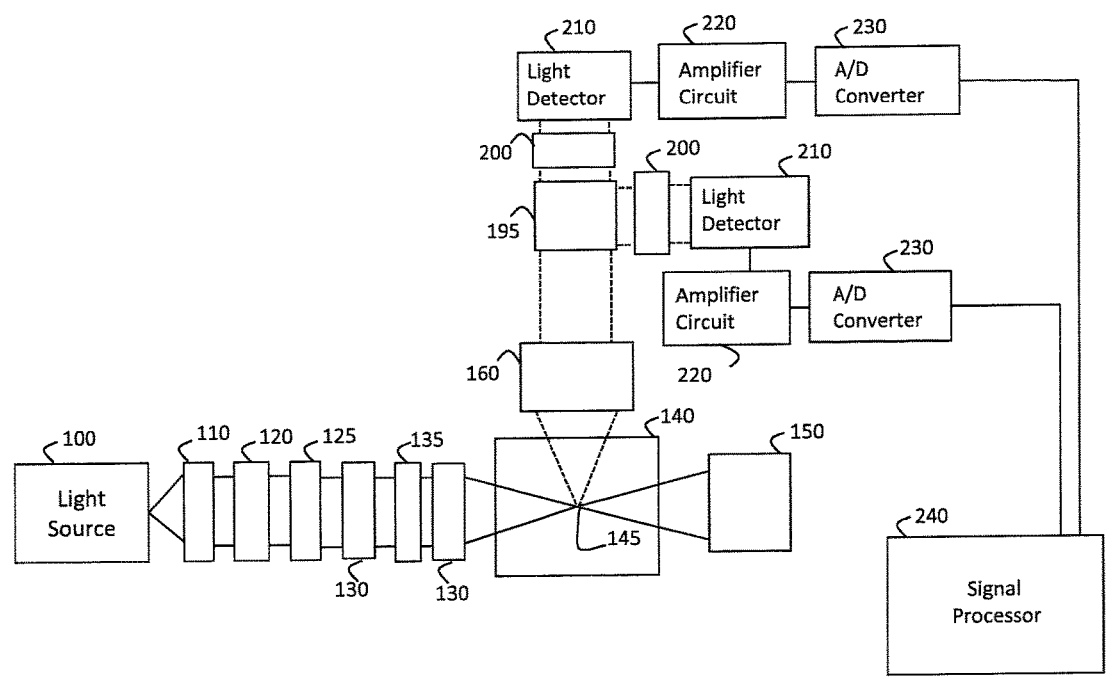
Figure 6:
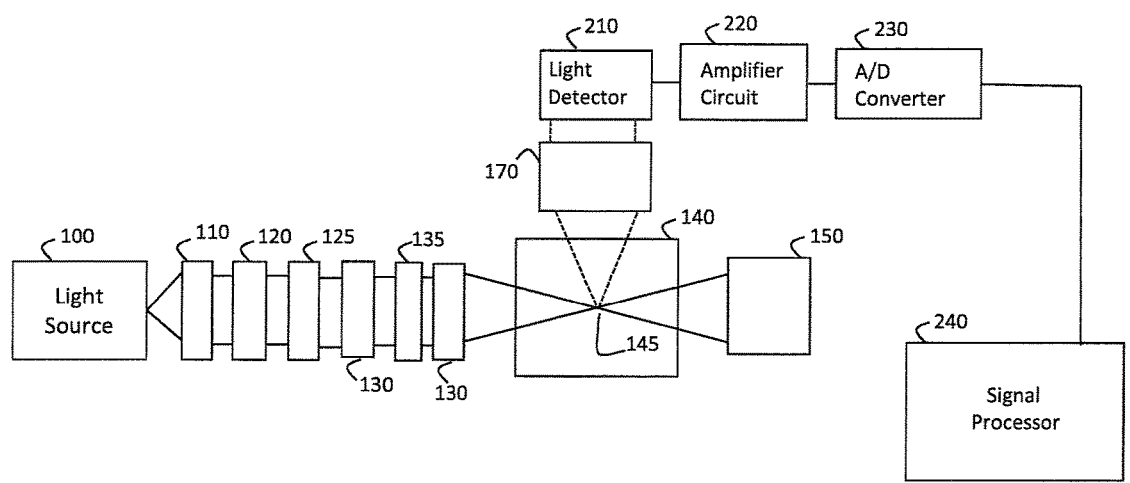
Figure 7:
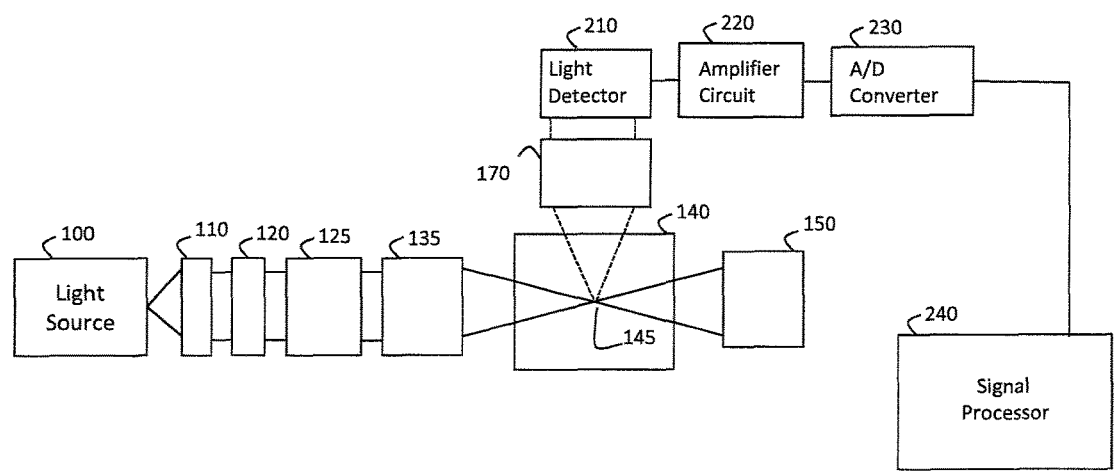

FIGS. 1-4 and 8 provide block diagrams outlining various embodiments of preferred optical detectors where linear depolarization measurements can be performed on individual particles using one or more excitation sources. FIG. 5 provides a block diagram outlining an embodiment of a preferred optical detector where circular depolarization measurements can be performed on individual particles using one or more excitation sources. FIG. 6 provides a block diagram outlining an embodiment of a preferred optical detector where circular intensity differential scattering or CIDS measurements can be performed on individual particles using one or more excitation sources. FIG. 7 provides a block diagram outlining an embodiment of a preferred optical detector where linear intensity differential scattering or LIDS measurements can be performed on individual particles using one or more excitation sources.

In each of the of the preferred optical detectors when measuring only particle size and polarized elastics scatter, a broad range of wavelengths can be used for excitation (e.g., 200-1500 nm). When measuring particle size, polarized elastic scatter, and fluorescence, then the excitation wavelengths need to be within the absorption bands of the endogenous fluorophores of interest such as 250-300 nm and 350-450 nm. Depending on the sensing configuration, the excitation source can be an edge emitting laser diode, vertical cavity surface emitting laser diode, light emitting diode or other laser source. Additionally, one or more of the sources can be configured to produce dual circularly or linearly polarized beams separated in space (e.g., vertically separated) using birefringent optics for illumination of single particles with two or more wavelengths and two polarization states for each wavelength at a time exciting the particle.

For flow rates exceeding 1 liter per minute, laser line generating optics may be used to generate a laser line thickness of from about 5 to about 300 micron, and a depth of field and laser line width that is at least two times (2×) the diameter of the inlet (aerosol orifice). For flow rates exceeding 20 liters per minute the use of a circular inlet may become restrictive and a rectangular inlet may be preferred. In cases of a rectangular inlet used to accommodate sampling flows exceeding 20 liters per minute, a laser line generating approach is preferred with the depth of field and laser line width adjusted to illuminate, at a minimum, the entire rectangular nozzle area. The above laser line generating approaches are to ensure complete illumination of the air sampling region with the purpose of near 100% percent illumination of the aerosol particles sampled. The laser line thickness is desired to be small as permissible with the optical design to ensure the highest possible aerosol count rate without illuminating more than one aerosol particle, in the size range of interest, so as to minimize particle coincidence.

In applications that require little pressure drop during sampling and/or low audible noise during operation the configurations described in the present invention can be operated without an aerosol inlet nozzle. In these configurations, the laser line illumination geometry and collection optics are used to interrogate a predefined region of the sampling volume providing a means for individual particle detection with low pressure drop and low audible noise through the use of axial fans as the vacuum source.

Various light collection geometries can be employed with different parameters applied for the different physical phenomena being measured. For particle sizing, using polarized elastic scatter detection, there are numerous approaches that can be taken and those skilled in the art are familiar with near forward scattering collection, side scatter collection, back scatter collection and wide angle collection using parabolic collectors. For polarized elastic detection, the process is sensitive to the angular collection angle and, therefore, aerosol sensing configurations that include mainly side scatter collection are preferred. For fluorescence detection, collection of fluorescence orthogonal to the direction of the light beam is preferred to minimize effects of stray light on the fluorescence signal(s).

Figure 1A:
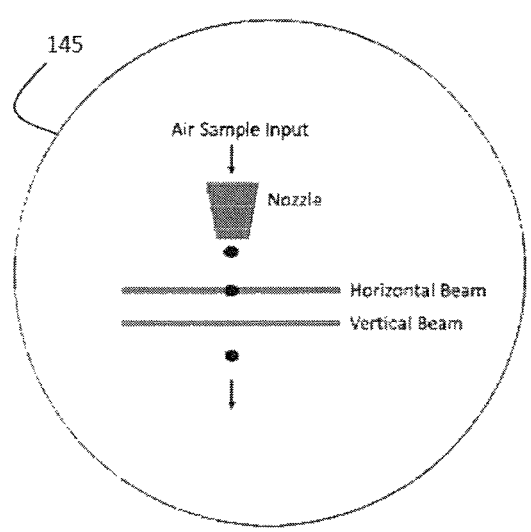

FIG. 1 is a schematic representation illustrating an optical detector including a linear depolarization detection configuration having a dual vertically and horizontally polarized beam source and a single detector with a horizontally polarized filter. Aerosol from the air surrounding the optical detector is drawn into the sensor cell 140 through an aerosol nozzle as shown in FIG. 1A or inlet port with no nozzle by a vacuum source (not shown) and is introduced into an optical viewing region 145. Any suitable vacuum source may be used. If an aerosol nozzle is employed the aerosol nozzle preferably is circular for flow rates below 20 liters per minute and can incorporate sheath flow in applications containing aerosol concentrations that would accelerate the fouling rate of the collection optics. For flow rates above 20 liters per minute, and a nozzle preferably is employed. The nozzle is preferably rectangular with the long side of the nozzle inlet following the light beam path and the short side orthogonal to the light beam.

The excitation source 100 is preferably a continuous source or modulated at 20 MHz or greater frequency and can be an edge emitting laser diode, vertical cavity surface emitting laser diode, light emitting diode or some other laser. The wavelength of excitation source 100 can be in the range of 200-1500 nm. Light emitted from source 100 is collimated using an aspheric lens 110. Depending on the source spatial filtering between the source 100 and the aspheric lens 110, or after lens 110 but before the aerosol cell 140 may be necessary. Collimated light is then introduced to beam shaping optics 125. The beam shaping optics 125 can be a single lens or group of lens designed to create a sheet of light at the aerosol nozzle region that is preferably from about 5 to about 300 micron in thickness and a depth of field and beam width that is preferably two times (2×) larger than the diameter of the inlet. In one embodiment, the beam shaping optics 125 can be a spherical lens and a cylinder lens designed to generate the above geometry. In another embodiment, only a cylinder lens is used for the beam shaping optics 125. In a further embodiment, the beam shaping optics 125 are comprised of top hat beam shaping optics which distributes the energy of a Guassian beam to a top hat profile. An example is a plano-convex lens that has a diffractive pattern located on its plane surface. Another example is the use of a single aspheric lens to convert the Guassian beam to a top hat profile. In another embodiment, the beam shaping optics 125 can be a single Powell lens or a spherical lens coupled with a Powell lens. When rectangular nozzles are used the beam shaping optics 125 can be comprised of the same components as listed above for circular nozzles but optical designs are preferably pursued that fulfill the depth of field requirements since the depth of field will be longer than the laser line width in these instances. The depth of field length in these instances can be greater than ten times (10×) the laser line width. To achieve near 100% illumination of sampled particles, within the desired size range, the width and depth of the sheet of light created by the beam shaping optics 125 should exceed, at a minimum, the dimensions of the rectangular nozzle.

Light from the beam optics 125 is introduced to a linear polarizer 120 with an extinction ratio preferably ranging from 100:1 to $10^7$:1. Certain sources such as edge emitting laser diodes and vertical cavity surface emitting laser diodes possess an inherent polarization ratio around 100:1 and depending on the accuracy requirements of the polarization measurement for a particular application the linear polarizer 120 can be omitted. After linear polarization, the collimated light is then introduced to a quarter wave retarder 130 to circularly polarize the beam before introduction to a birefringent crystal 135. Examples of birefringent crystals that can be used include yttrium vandate, barium borate, calcite and rutile. The introduction of the circularly polarized light to the birefringent crystal 135 produces vertically and horizontally polarized beams of equal intensity and separated in space (e.g., vertically separate) by a certain distance depending on the length of the crystal. In various configurations a separation of 250 micron to 1000 micron is preferred.

The light beams are then introduced into the optical viewing region 145 as seen in FIG. 1A. Because spatially separated beams enter the optical sensing zone 140, the optical viewing region 145 includes two spatially separated illumination points or areas, one for each beam as see in FIG. 1A. Particles are illuminated, one at a time, in each of the two spatially separated illumination areas of region 145 by the corresponding beam with an aerosol migration time 100 nanoseconds to 10 microseconds depending on the nozzle dimensions and whether a nozzle is used, sample flow rate, and laser line thickness. Light exiting this region in the forward direction is collected using a light trap 150. Preferably, the illumination area illuminated by the horizontally polarized beam is positioned below the illumination area illuminated by the vertically polarized beam as seen in FIG. 1A.

In the preferred embodiment illustrated in FIG. 1, light emitted as polarized elastic scatter is collected on one side of the aerosol cell 140 and orthogonal to the light beam. For particle sizing and polarized elastic scatter analysis, collection optic 170 is preferably used to collect elastically scattered light. Depending on the sensitivity of the photodetector 210 employed, various types of collection optics and angular collection ranges can be used. For the most sensitive photodetectors with large active areas, such as, photomultiplier tubes, silicon photomultipliers or avalanche photodiodes the collection optic 170 can be omitted in some instances. For configurations requiring a collection optic 170, an aspheric collector lens, parabolic collectors, or cylinder lens can be used. The angular collection range can be controlled by the size of the aspheric or cylinder lens or the geometry of the parabolic collectors. Those skilled in the art are aware of numerous approaches using aspheric lens or parabolic collectors as the collection optic 170. Which collection optic 170 to use depends on the sensitivity of the photo-detector 210 employed and application. For applications where the aerosol concentration sampled is considered high, it is preferred to use a collection optic 170 that is easy to clean and would possess a low fouling rate from sampled aerosol. In this case collection optic 170 may be omitted or an aspheric lens can be used instead of parabolic collectors as the collection optic 170.

For linear depolarization detection and particle sizing, light that has scattered orthogonally to the laser source first passes through a horizontally polarized filter 207 and is then introduced to collection optic 170 and subsequently to light detector 210. The light detector 210 can be a silicon photodiode, gallium arsenide photodiode, avalanche photodiode, silicon photomultiplier, photomultiplier tube or arrays of these types of detectors. The type of detector will vary depending on the collection optic 170 used, the amount of scattered light excepted per aerosol event, the dynamic range of the detector, and the detector's cut-off frequency or response time. The signal produced from light detector 210 is then introduced to an amplifier circuit 220 whereby a 100 nanosecond to 10 microsecond current pulse is first converted to an analog voltage and then to a digital signal using an analog-to-digital converter 230. The signal from 230 is then introduced to the signal processor 240 for analysis. The signal processor 240 can be a microcontroller, digital signal processor, field programmable gate array or a microcomputer, as would be readily understood by one skilled in the field of signal processing.

As previously explained, for the configuration illustrated in FIG. 1, single aerosol events are introduced to two illuminations areas in the optical viewing region 145 separated by a predetermined distance as seen in FIG. 1A. The first illumination region is preferably illuminated by the horizontally polarized beam with a laser line thickness of 5-300 micron. The second illumination region is preferably illuminated by the vertically polarized beam of equal thickness (i.e., a laser line thickness of 5-300 micron) and laser intensity separated by a preferred distance of approximately 250-1000 micron. As the particle traverses the beams, two 100 nanosecond to 10 microsecond current pulses are produced and processed.

The amplifier circuits 220 for each channel can be configured to perform analog signal processing functions. The analog input bandwidth for the amplifier circuits 220 for each channel can be configured to capture the fastest expected current pulses. The pulse time is primarily a function of the aerosol particle's migration time through the optical viewing region 145 and is expected to be in the range of 100 nanoseconds to 10 microseconds. Additional analog signal processing functions include the triggering of a pulse detector circuit when an analog voltage level from the detection channels exceeds a preprogrammed level, integration and holding of light detector pulse for each detection event, production of a pulse height level for each detection channel, the use of one or more amplifier stages for each detection channel to capture the entire signal range for particles ranging in size from submicron in aerodynamic diameter to 25 micron or larger, and the production of an analog to digital conversion signal for each of the two detection events.

For both particle sizing and linear depolarization detection, the signal processor 240 is preferably configured to receive digital signals from the two detections events that occurred as the single particle traversed the horizontally and vertically polarized beams. For particle sizing, the first detection event is preferably used to size the particle and pulse height analysis is performed on each of the aerosol events occurring in the first and second illumination points or areas in the optical viewing region 145. For linear depolarization detection, the amplitudes of each detection per aerosol event is used for the depolarization measurement. The degree of depolarization for each aerosol event can be calculated by performing one of the calculations below:

$$\delta_N=[I_V]/[I_H+I_V] \text{ or } \delta=I_{HV}/I_{HH}$$

The linear depolarization value is then preferably binned with the particle size for each aerosol event. Using particle size and linear depolarization value data for each aerosol particle, preferably a comparison can be made to a library of aerosol types from the previous measurements of known aerosols that include bacterial spores, vegetative cells, viruses, viral aggregates, protein toxin aggregates, fungal particles, pollen particles, man-made biological particles and non-biological aerosols such as salt particles, water droplets, dust particles, organic carbon particles and other relevant non-biological particles depending on the application. With the library and unknown particle data, polarized elastic scatter plots can be generated as a function of particle size permitting the detection and classification of biological and non-biological particles.

FIG. 9 illustrates the detection event for a single particle for the linear depolarization configuration described above. In this embodiment, the single particle traverses two beams, first a horizontally polarized beam then a vertically polarized beam. As the particle traverses each beam, the particle emits polarized elastically scattered light producing two signals per aerosol particle event. FIG. 9 shows data for a single aerosol event and a single detector. The data represents the linear depolarization response for a 3 micron aerodynamic diameter *Bacillus globigii* spore aggregate. The particle was produced using an ECBC inkjet aerosol generator. The degree of depolarization can be calculated by performing one of the calculations above.

Figure 10:
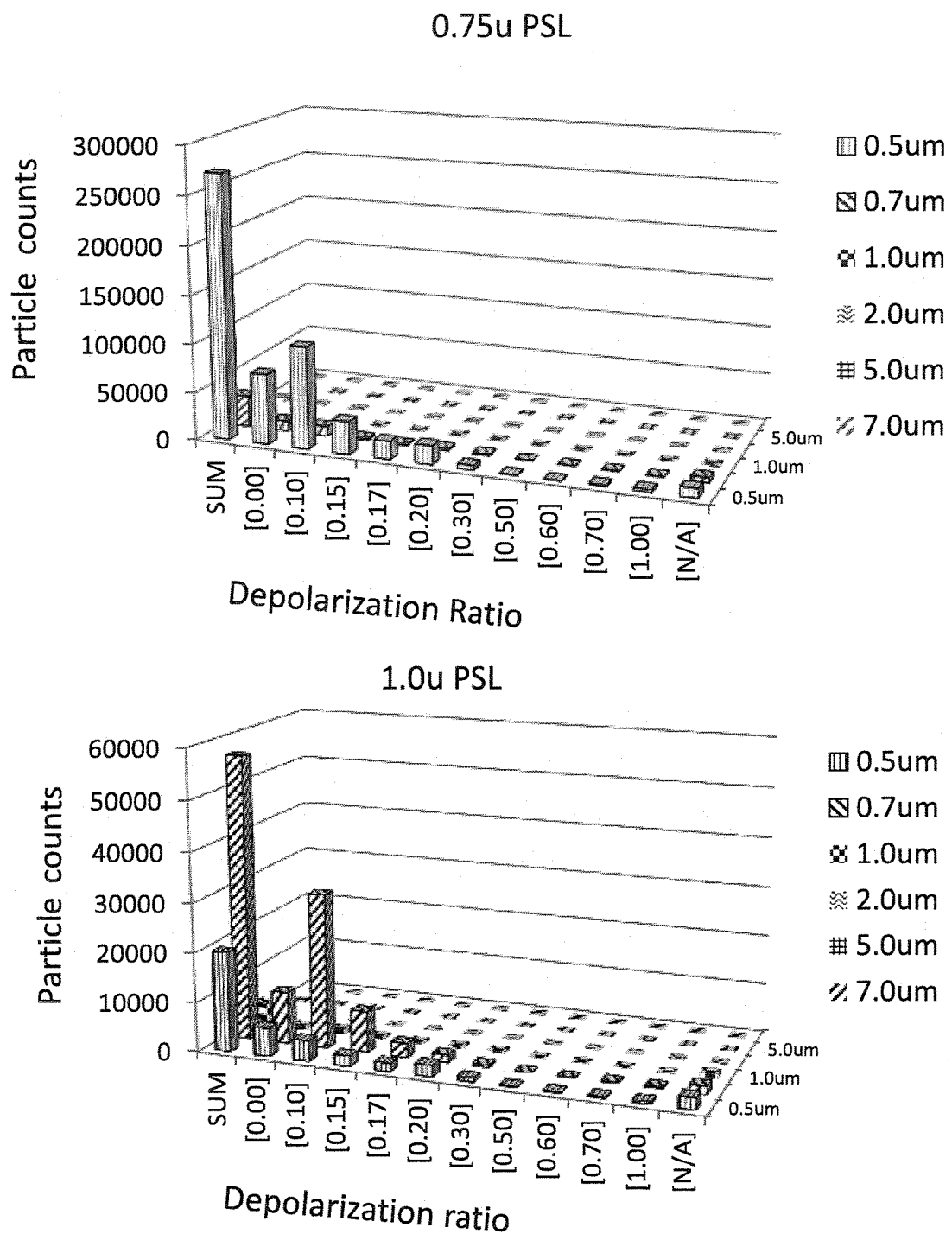
Figure 11:
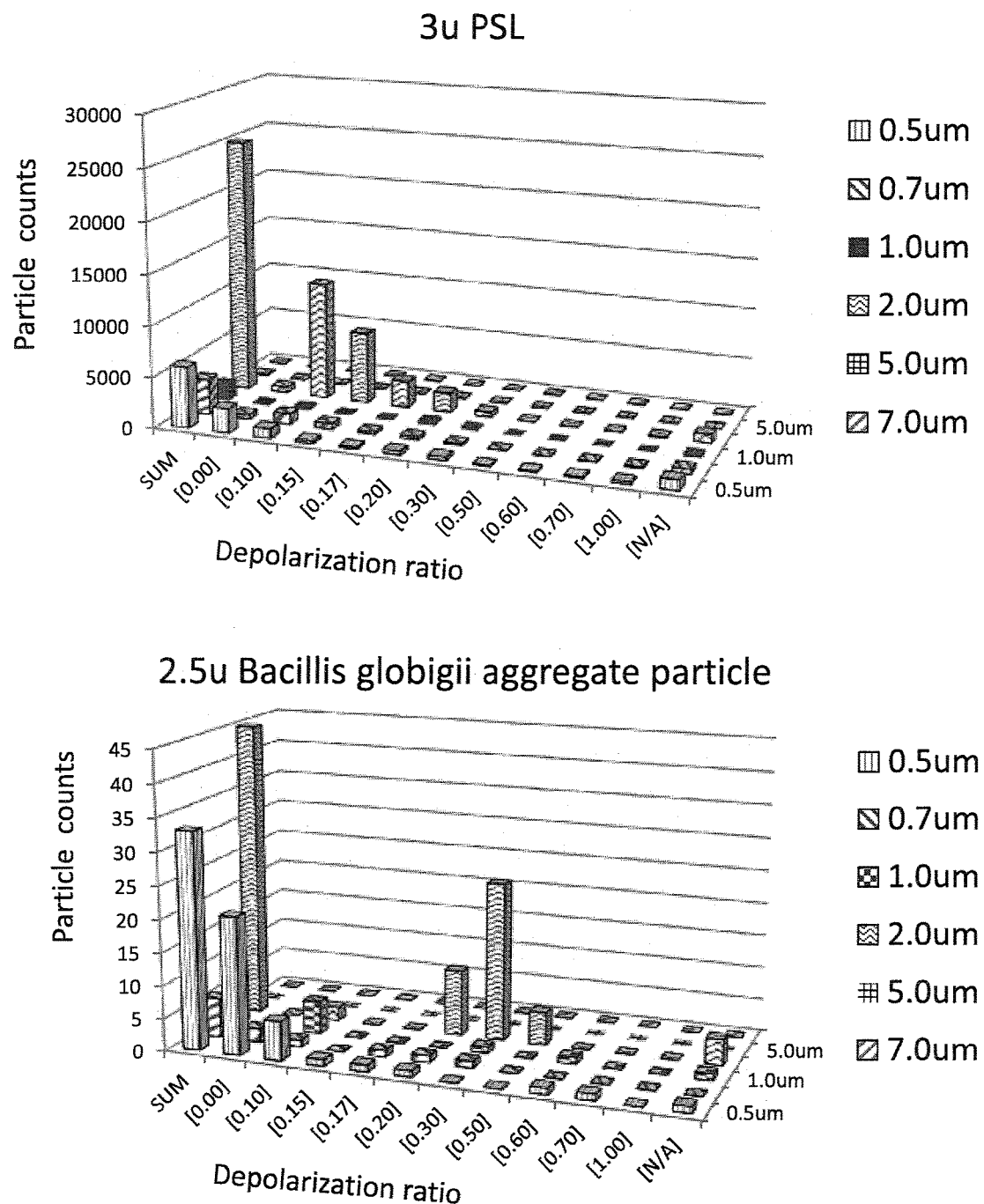

FIGS. 10 and 11 illustrate the linear depolarization response where the degree of depolarization is determined by dividing the scatter intensity collected from a horizontally polarized filtered signal and a horizontally polarized excitation source by the scatter intensity collected from a horizontally polarized filtered signal and a vertically polarized excitation source. This data shows 6 particle size channels with the following channel ranges: 0.5-0.7 micron, 0.7-1 micron, 1-2 micron, 2-5 micron, 5-7 micron, and >7 micron. Ten polarization ratio increments are used for each particle size range giving a total of 60 channels with the signal processor having programmable depolarization ratio increments. Aerosol particle events are detected and then binned into one of the 60 channels depending on their size and degree of linear depolarization. For illustration of the ability to classify particle types, 3 different sizes on polystyrene microspheres (0.7, 1.0 and 3.0 micron diameter) and a 2.5 micron diameter *Bacillus globigii* spore aggregate are provided as examples. As can be seen from the graphs, the particle types can be classified based on their size and degree of depolarization with the polystyrene microspheres giving a lower depolarization response (0-0.2) than the *Bacillus* spore aggregate (0.2-0.5).

Figure 12:
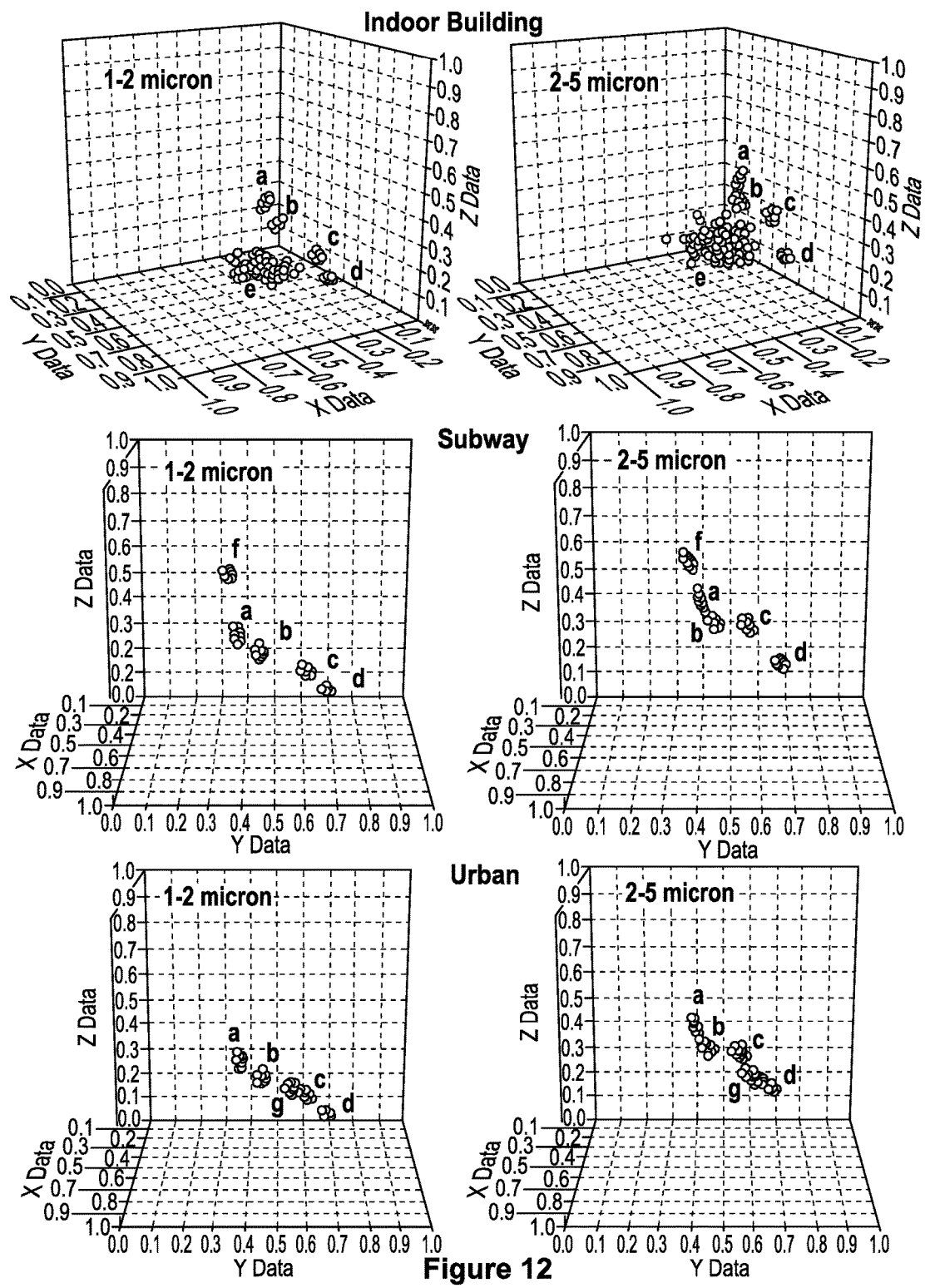

FIG. 12 illustrates additional linear depolarization responses using the same ratio measurement as in FIGS. 10 and 11 and the use of depolarization ratio distributions to classify particles of interest from commonly encountered particles from different environments. Three different environments are provided as examples: an indoor building, a subway platform and an urban background. The 3D scatter plots represent 3 depolarization ratios for a given particle size range. Each sphere in the 3D scatter plot represents 10 liters of air sample and was collected using a sensor with a 100 liter per minute sampling rate or 6 seconds of aerosol data. Four biological class types are also applied in the 3D scatter plot. They are dry disseminated *Bacillus globigii* spore (spore simulant), dry disseminated ovalbumin (toxin simulant), *Erwinia herbicola* (vegetative simulant), and MS2 virus (viral simulant). The coordinates for the 3 axes are obtained by selecting three depolarization increments at a defined particle size range. Particle counts for each of the 3 selected depolarization increments for a 10 liter sampling rate are divided by the sum of the total particle counts for each of the 3 depolarization increments at a defined particle size range. The ratio for each depolarization increment is then used as one of the three coordinates for the 3D scatter plot. In FIG. 12, the four biological threat class types are labeled a through d, representing dry spore, dry toxin, viral and vegetative classes respectively. FIG. 12 provides 3D scatter plots for 2 particle size ranges, 1-2 micron and 2-5 micron, for each background environment. Air samples representing the background environments are labeled e through g representing indoor building, a subway platform, and an urban background respectively. As can be seen from the plots, the linear depolarization approach applied in this embodiment provides a very useful method for discriminating all four disseminated biological threat types from relevant operational environments. The approach provides a rapid near real-time early warning capability against biological threats and the ability to classify biological threat types providing end users with additional options for applying countermeasures that reduce the aerosol spread in a facility or subway system and a more rapid application of prophylactics.

FIG. 13 illustrates additional linear depolarization responses using the same ratio measurement as in FIGS. 10 and 11 and 3D scatter analysis approach. This data illustrates a wet disseminated or nebulized *Bacillus globigii* spore sample in which nearly the entire sample aerosolized is comprised of individual spores. The graph labeled h provides the particle size distribution of the sample aerosolized. The aerosol distribution was measured using a TSI 3321 Aerodynamic Particle Sizer and shows an aerodynamic median diameter of 0.819 micron with a geometric standard deviation of 1.20, or, a monodisperse population. As in FIG. 12, the four biological threat class types are labeled a through d, representing dry spore, dry toxin, viral and vegetative classes respectively. The nebulized *Bacillus* spore sample is labeled i in the scatter plot. This example illustrates the effectiveness of the depolarization approach to detect and classify single *Bacillus* spores which is very difficult for currently available LIF based biological aerosol detectors.

Figure 2:
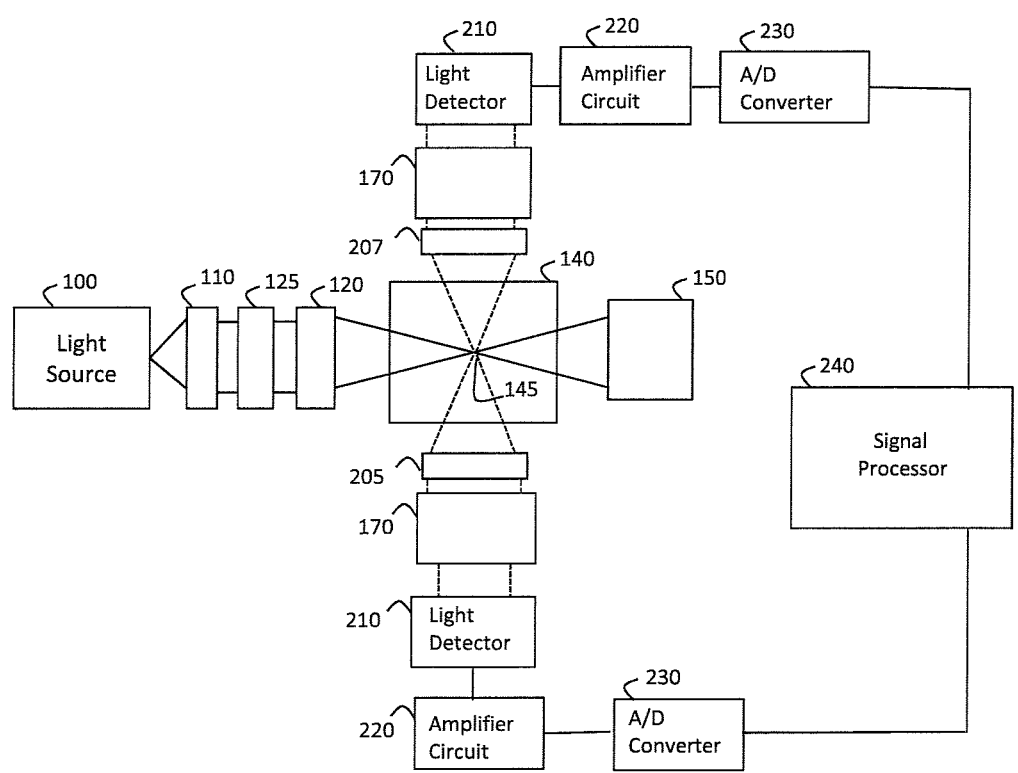
Figure 3:
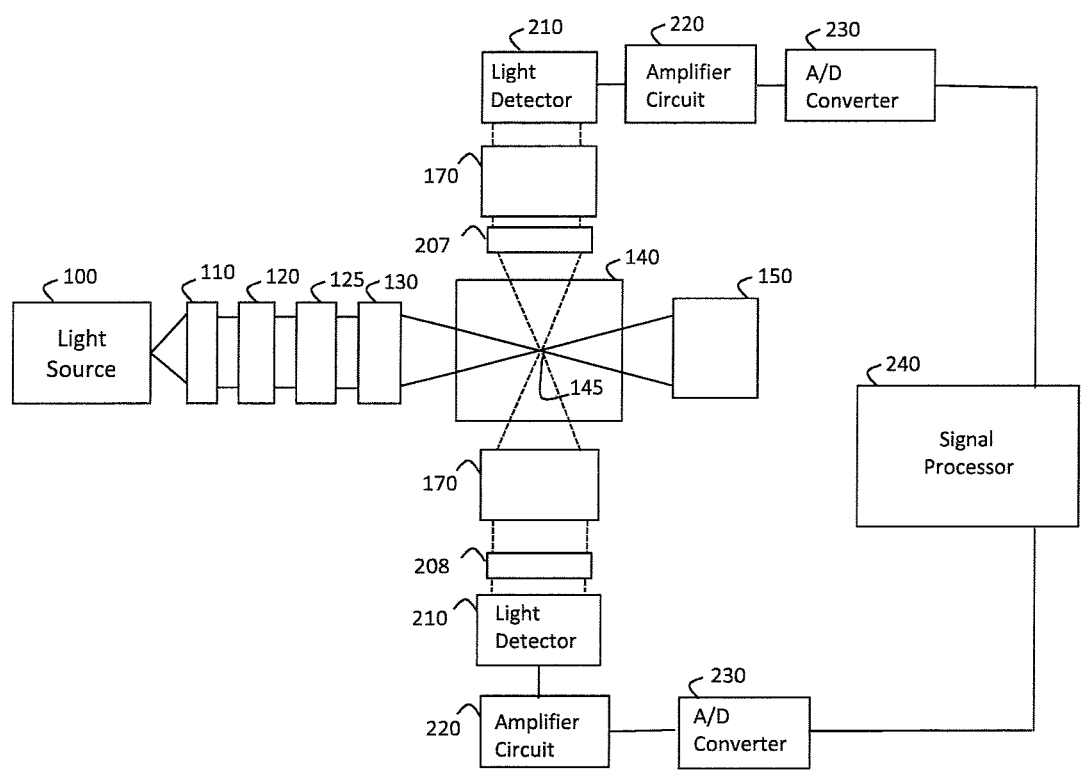
Figure 4:
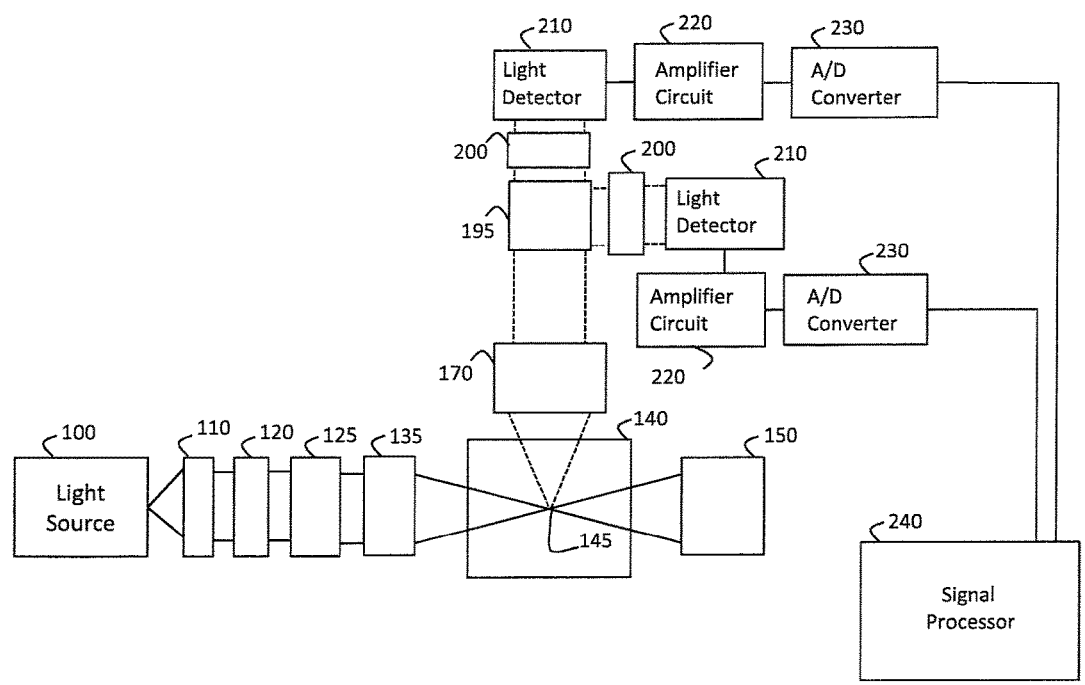

FIG. 2 is a schematic representation illustrating a preferred optical detector including a linear depolarization detection configuration having a single horizontally polarized beam source and two detectors with one having a horizontally polarized filter and the other a vertically polarized filter. Aerosol is drawn into the sensor cell 140 through an aerosol nozzle as shown in FIG. 1A or inlet port with no nozzle by a vacuum source (not shown) and is introduced into an optical viewing region 145 in a similar manner as described for FIG. 1. The illumination scheme and detection scheme are different for this configuration from that utilized in FIG. 1. The excitation source 100 is preferably a continuous source or modulated at 20 MHz or greater frequency and can be an edge emitting laser diode, vertical cavity surface emitting laser diode, light emitting diode or some other laser. The wavelength of excitation source 100 can be in the range of 200-1500 nm. Light emitted from source 100 is collimated using an aspheric lens 110. Depending on the source, spatial filtering between the source 100 and the aspheric lens 110, or after lens 110 but before the aerosol cell 140 may be necessary. Collimated light is then introduced to beam shaping optics 125, as described in FIG. 1, followed by a horizontally polarized filter 120.

In the embodiment illustrated in FIG. 2, light emitted as polarized elastic scatter is collected on both sides of the aerosol cell 140 and orthogonal to the light beam. For particle sizing and polarized elastic scatter analysis, the same collection optics and detector components as those described for the embodiment illustrated in FIG. 1 can be applied. In this embodiment, scattered horizontally polarized light is collected by passing through the horizontally polarized filter 205 followed by the collection optic 170. Scattered vertically polarized light is collected by passing through the vertically polarized filter 207 followed by collection optic 170. In this embodiment, scatter amplitudes from both vertically and horizontally polarized light using horizontally polarized excitation is used for measuring linear depolarization. Similar detectors and electronics as that described for the embodiment illustrated in FIG. 1 applies for this configuration except two light scatter pulses occurring simultaneously corresponding to the scatter amplitudes from vertically and horizontally polarized light are used for depolarization measurement as the optical viewing region 145 has a single illumination area or point.

For particle sizing, the horizontally polarized scatter signal is used to size the particle and pulse height analysis is performed on the scatter amplitudes from vertically and horizontally polarized light. For linear depolarization detection, the amplitudes from each detection event for the two detectors is used for the depolarization measurement. The degree of depolarization for each aerosol event can be calculated by performing one of the calculations below:

$$\delta_N = [I_V]/[I_H + I_V] \text{ or } \delta = I_{HV}/I_{HH}$$

The linear depolarization value is then binned with the particle size for each aerosol event. Using particle size and linear depolarization value data for each aerosol particle a comparison is preferably made to a library of aerosol types from the previous measurements of known aerosols that include bacterial spores, vegetative cells, viruses, viral aggregates, protein toxin aggregates, fungal particles, pollen particles, man-made biological particles and non-biological aerosols such as salt particles, water droplets, dust particles, organic carbon particles and other relevant non-biological particles depending on the application. With the library and unknown particle data, polarized elastic scatter plots can be generated as a function of particle size permitting the detection and classification of biological and non-biological particles.

FIG. 3 is a schematic representation illustrating a preferred optical detector including a linear depolarization detection configuration having a dual vertically and horizontally polarized beam source and a single detector with a horizontally polarized filter and an orthogonal fluorescence detection channel. The configuration is the same as that described for the embodiment illustrated in FIG. 1 except for the additional fluorescence detection channel 208 and the corresponding collection optics 170, light detector 210, amplifier 220 and analog to digital converter 230.

When measuring particle size, polarized elastic scatter, and fluorescence, the excitation wavelengths need to be within the absorption bands of the endogenous fluorophores of interest such as 250-300 nm and 350-450 nm. These excitation wavelength ranges correspond to the absorption bands to one or more endogenous fluorophores commonly encountered in biological particles, which include, but are not limited to aromatic amino acids, NADH, flavins, chlorophylls, and sideophores. For the fluorescence detection channel, similar detection electronics and detectors as that described in the above embodiments can be used with an additional fluorescence filter 208 for passing a band of light that is matched with the emission wavelengths of the desired endogenous fluorophores. In this embodiment, both the linear depolarization value obtained for each particles and the presence or absence of fluorescence and the fluorescence intensity can be used for classification of biological particles from non-biological particles and to classify biological types from one another.

FIG. 4 is a schematic representation illustrating a preferred optical detector including a linear depolarization detection configuration having a vertically and horizontally polarized beam source, a polarizing beam splitter and two detectors for detecting parallel and perpendicularly polarized scatter. In this embodiment, instead of two detectors employing horizontally and vertically polarized filters a polarizing beam splitter 195 is used for separating the two polarizations so that measurement of the scatter intensity of both vertically and horizontally polarized light can be performed. An optional focusing lens 200 can be used to focus the scattered light onto a light detector 210. The same signal processing steps as outlined in the embodiment illustrated in FIG. 2 can be applied.

FIG. 5 is a schematic representation illustrating a preferred optical detector including a circular depolarization detection configuration having a dual left handed and right handed circularly polarized beam source, a polarizing beam splitter and two detectors for detecting parallel and perpendicularly polarized scatter. In this embodiment, the dual polarized beam as that described in the embodiment illustrated in FIG. 1 is used except an additional quarter wave retarder 130 is employed after the birefringent crystal 135 to create dual right handed and left handed circularly polarized beams.

With circular depolarization detection, the normalized depolarization of light scattered from a particle is given by the relationship:

$$\delta_{+C}=[I_\perp]/[I_\parallel+I_\perp]$$

$$\delta_{-C}=[I_\parallel]/[I_\parallel+I_\perp]$$

Where $\delta_{+C}$ represents circular depolarization when using right handed polarized light as the illumination source, $\delta_{-C}$ represents circular depolarization when using left handed polarized light as the illumination source, $I_\perp$ represents the scatter intensity for perpendicularly polarized light and $I_\parallel$ represents the scatter intensity for parallel polarized light. In this embodiment, circular depolarization measurements can be performed on single particles using both left handed and right handed circularly polarized excitation. The same detectors and electronics as the embodiment illustrated in FIG. 4 can be used.

Signal processing for this embodiment involves measuring the polarized scatter intensity of parallel and perpendicularly polarized light for each illumination event per aerosol particle and then calculating the left handed and right handed circular depolarization ratios for each particle. The circular depolarization values are then binned with the particle size for each aerosol event. Particle size and circular depolarization value data for each aerosol particle is then compared to a library of aerosol types from the previous measurements of known aerosols that include bacterial spores, vegetative cells, viruses, viral aggregates, protein toxin aggregates, fungal particles, pollen particles, man-made biological particles and non-biological aerosols such as salt particles, water droplets, dust particles, organic carbon particles and other relevant non-biological particles depending on the application. With the library and unknown particle data, polarized elastic scatter plots can be generated as a function of particle size permitting the detection and classification of biological and non-biological particles.

FIG. 6 is a schematic representation illustrating a preferred optical detector including a circular intensity differential scattering detection (CIDS) configuration having a dual left handed and right handed circularly polarized beam source and a single detector. The excitation source for this embodiment is similar to the embodiment illustrated in FIG. 5. A single detector scheme similar to that illustrated in FIG. 1 is used capturing polarized elastic scatter signals and scatter intensities are measured using both left handed and right handed circular polarized excitation per aerosol particle. No filter is used on the detection channel so unfiltered scatter signals are collected for each illumination event. The circular intensity differential scattering (CIDS) value for each aerosol event can be determined using the following equation:

$$[I_L - I_R]/[I_L + I_R],$$

Where $I_L$ is the light scattered intensity when the incident beam is left circularly polarized and $I_R$ is the light scattered intensity when the incident beam is right circularly polarized. The current pulses produced from the detection events are used for measuring the CIDS value for each particle. The CIDS value is then binned with the particle size for each aerosol event. Using particle size and CIDS value data for each aerosol particle, a comparison can be made to a library of aerosol types from the previous measurements of known aerosols that include bacterial spores, vegetative cells, viruses, viral aggregates, protein toxin aggregates, fungal particles, pollen particles, man-made biological particles and non-biological aerosols such as salt particles, water droplets, dust particles, organic carbon particles and other relevant non-biological particles depending on the application. With the library and unknown particle data, polarized elastic scatter plots can be generated as a function of particle size permitting the detection and classification of biological and non-biological particles.

FIG. 7 is a schematic representation illustrating a preferred optical detector including a linear intensity differential scattering detection (LIDS) configuration having a dual vertically and horizontally polarized beam source and a single detector. The LIDS configuration is identical to the CIDS configuration except no quarter wave retarder 130 is used. The linear intensity differential scattering (LIDS) value for each aerosol event can be determined using the following equation:

$$[I_H - I_V]/[I_H + I_V],$$

Where $I_H$ is the light scattering intensity when the incident beam is horizontally polarized and $I_V$ is the light scattered when the incident beam is vertically polarized. The current pulses produced from the detection events are used for measuring the LIDS value for each particle. The LIDS value is then binned with the particle size for each aerosol event. Using particle size and LIDS value data for each aerosol particle, a comparison can be made to a library of aerosol types from the previous measurements of known aerosols that include bacterial spores, vegetative cells, viruses, viral aggregates, protein toxin aggregates, fungal particles, pollen particles, man-made biological particles and non-biological aerosols such as salt particles, water droplets, dust particles, organic carbon particles and other relevant non-biological particles depending on the application. With the library and unknown particle data, polarized elastic scatter plots can be generated as a function of particle size permitting the detection and classification of biological and non-biological particles.

Figure 8:
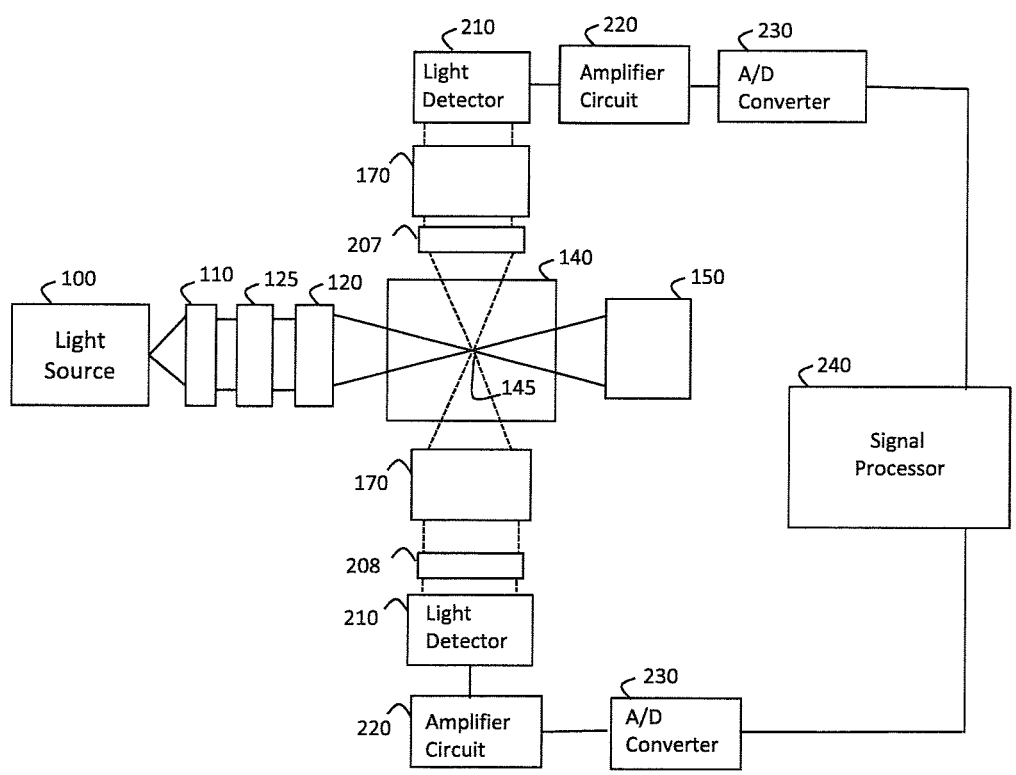

FIG. 8 is a schematic representation illustrating a preferred optical detector including a linear depolarization detection configuration having a single horizontally polarized beam source and a single detector having a vertically polarized filter 207 and an orthogonal fluorescence detection channel 208. As described in FIG. 2 a single horizontally polarized beam source is used to illuminate single particles in the sample stream passing through the optical viewing region 145. In this configuration, only depolarized scatter events are detected with the degree of depolarization being a function of particle size and morphology. Using the fluorescence detection channel 208, particle auto-fluorescence is also measured for each depolarized scatter event. When measuring depolarized elastic scatter and fluorescence, the excitation wavelengths need to be within the absorption bands of the endogenous fluorophores of interest such as 250-300 nm and 350-450 nm. These excitation wavelength ranges correspond to the absorption bands to one or more endogenous fluorophores commonly encountered in biological particles, which include, but are not limited to aromatic amino acids, NADH, flavins, chlorophylls, and sideophores. For the fluorescence detection channel, similar detection electronics and detectors as that described in the above embodiments can be used with an additional fluorescence filter 208 for passing a band of light that is matched with the emission wavelengths of the desired endogenous fluorophores. In this embodiment, both depolarized elastic scatter intensity obtained for each particle and the presence or absence of fluorescence and the fluorescence intensity can be used for classification of biological particles from non-biological particles and to classify biological types from one another.

The forgoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents. The claims are not limited to the preferred embodiments and have been written to preclude such a narrow construction using the principles of claim differentiation.

Further, in describing representative embodiments of the present invention, the specification may have presented the preferred method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of steps set forth in the specification should not be construed as limitations on the claims. In addition, the claims directed to the method and/or process of the present invention should not be limited to the performance of their steps in the order presented, and one skilled in the art can readily appreciate that the sequences may be varied and still remain within the spirit and scope of the present invention.

I claim:

1. A method of detecting and classifying single airborne particles, said method comprising:
   (a) directing an airborne sample having a plurality of airborne particles into an optical sensing zone of an optical detector, the airborne sample being taken from an environment surrounding the optical detector;

(b) illuminating a single airborne particle in the optical sensing zone with a first polarized light beam;
(c) detecting elastic light scatter resulting from the illumination of the single airborne particle with the first polarized light beam;
(d) determining, using the detected elastic light scatter resulting from the illumination of the single airborne particle with the first polarized light beam, each of the following:
  (i) a size of the single airborne particle; and,
  (ii) a first value for the single airborne particle wherein the first value is one of a depolarization value for the single airborne particle and an intensity differential elastic scattering value for the single airborne particle; and,
(e) determining at least one characteristic of the single airborne particle based on the size of the single airborne particle and the first value for the single airborne particle.

2. The method of claim 1, wherein:
(a) the single airborne particle has an aerodynamic diameter of no greater than 10 microns.

3. The method of claim 1, wherein:
(a) the at least one characteristic identifies the single airborne particle as biological or non-biological.

4. The method of claim 1, wherein:
(a) the at least one characteristic identifies the single airborne particle as a specific type of biological particle.

5. The method of claim 1, further including the steps of:
(a) illuminating the single airborne particle in the optical sensing zone with a second polarized light beam wherein the second polarized light beam is spaced a predetermined distance from the first polarized light beam, the first polarized light beam is a horizontally polarized light beam and the second polarized light beam is a vertically polarized light beam; and,
(b) detecting elastic light scatter resulting from the illumination of the single airborne particle with the horizontally polarized light beam and the vertically polarized light beam.

6. The method of claim 5, further including the step of:
(a) prior to detecting step of claim 5, passing elastic light scatter resulting from the illumination of the single airborne particle with the horizontally polarized light beam and the vertically polarized light beam through a horizontal polarization filter.

7. The method of claim 6, wherein:
(a) the first value is a linear depolarization value.

8. The method of claim 1, further including the steps of:
(a) illuminating the single airborne particle in the optical sensing zone with a second polarized light beam wherein the second polarized light beam is spaced a predetermined distance from the first polarized light beam, the first polarized light beam is a right handed circularly polarized light beam and the second polarized light beam is a left handed circularly polarized light beam.

9. The method of claim 8, wherein:
(a) the first value is one of a circular depolarization value and circular intensity differential scattering value.

10. The method of claim 1, wherein:
(a) if the first value is a depolarization value, determining the depolarization value by using at least one of the following equations:
  (i) $\delta_N = [I_V]/[I_H + I_V]$ where $\delta N$ represents normalized depolarization, $I_H$ represents the elastic scatter intensity for horizontally polarized light and is the same as the polarization state of the illumination beam and $I_V$ represents the elastic scatter intensity for vertically polarized light;
  (ii) $\delta = I_{HV}/I_{HH}$ where $\delta$ represents depolarization, $I_{HH}$ represents the elastic scatter intensity for horizontally polarized light and horizontally polarized incident beam, $I_{HV}$ represents the elastic scatter intensity for horizontally polarized light and a vertically polarized incident beam;
  (iii) $\delta_{+C} = [I_\perp]/[I_\parallel + I_\perp]$ where $\delta_{+C}$ represents circular depolarization when using right handed circularly polarized light as the illumination source, $I_\perp$ represents the elastic scatter intensity for perpendicularly polarized light and $I_\parallel$ represents the elastic scatter intensity for parallel polarized light;
  (iv) $\delta_{-C} = [I_\parallel]/[I_\parallel + I_\perp]$ where $\delta_{-C}$ represents circular depolarization when using left handed circularly polarized light as the illumination source, $I_\perp$ represents the elastic scatter intensity for perpendicularly polarized light and $I_\parallel$ represents the elastic scatter intensity for parallel polarized light; and,
(b) if the first value is an intensity differential elastic scattering value, determining the intensity differential elastic scattering value by using at least one of the following equations:
  (i) $[I_L(\theta) - I_R(\theta)]/[I_L(\theta) + I_R(\theta)]$ where $I_L(\theta)$ is the light scattered at angle $\theta$ when the incident beam is left circularly polarized and $I_R(\theta)$ is the light scattered at angle $\theta$ when the incident beam is right circularly polarized; and,
  (ii) $[I_H(\theta) - I_V(\theta)]/[I_H(\theta) + I_V(\theta)]$ where $I_H(\theta)$ is the light scattered at angle $\theta$ when the incident beam is horizontally polarized and $I_V(\theta)$ is the light scattered at angle $\theta$ when the incident beam is vertically polarized.

11. A method of detecting and classifying single airborne particles, said method comprising:
(a) using a vacuum source to pull an airborne sample having a plurality of airborne particles into an optical sensing zone of an optical detector from an environment surrounding the optical detector;
(b) illuminating a single airborne particle in the optical sensing zone with a horizontally polarized light beam;
(c) illuminating the single airborne particle in the optical sensing zone with a vertically polarized light beam, wherein the vertically polarized light beam illuminates the single airborne particle before or after the horizontally polarized light beam illuminates the single airborne particle;
(d) detecting elastic light scatter resulting from the illumination of the single airborne particle with the horizontally polarized light beam and the vertically polarized light beam; and,
(e) prior to the detecting step of paragraph (d), passing elastic light scatter resulting from the illumination of the single airborne particle with the horizontally polarized light beam through a horizontal polarization filter.

12. The method of claim 11, including the further step of:
(a) prior to the detecting step of paragraph (d) of claim 11, passing elastic light scatter resulting from the illumination of the single airborne particle with the vertically polarized light beam through a horizontal polarization filter.

13. The method of claim 12, including the further step of:
(a) determining, using the detected elastic light scatter resulting from the illumination of the single airborne particle, each of the following:
  (i) a size of the single airborne particle; and,
  (ii) a linear depolarization value for the single airborne particle; and,
(b) determining at least one characteristic of the single airborne particle based on the size of the single airborne particle and the linear depolarization value for the single airborne particle.

14. The method of claim 12, further including the step of:
(a) directing elastic light scatter passing through the horizontal polarization filter to a single light detector.

15. The method of claim 11, including the further step of:
(a) prior to the detecting step of paragraph (d) of claim 11, passing elastic light scatter resulting from the illumination of the single airborne particle with the vertically polarized light beam through a vertical polarization filter.

16. The method of claim 11, wherein:
(a) the single airborne particle has an aerodynamic diameter in a range of 0.5 to 1.5 microns.

17. The method of claim 11, wherein:
(a) the single airborne particle has an aerodynamic diameter no greater than 10 microns.

18. The method of claim 11, further including the step of:
(a) passing elastic light scatter resulting from the illumination of the single airborne particle with the horizontal polarized light beam and the vertically polarized light beam through an orthogonal fluorescence detection channel wherein the orthogonal fluorescence detection channel is disposed on one side of the optical sensing zone and the horizontal polarization filter is disposed on an opposite side of the optical sensing zone.

19. A single airborne particle optical analyzer for detecting and classifying single airborne particles, said single airborne particle optical analyzer comprising:
(a) an optical sensing zone;
(b) a vacuum source for pulling an airborne sample having a plurality of airborne particles into an optical sensing zone of an optical detector from an environment in which the optical sensing zone is located;
(c) means for illuminating a single airborne particle in the optical sensing zone with at least one polarized light beam;
(d) a light detector for detecting elastic light scatter resulting from the illumination of the single airborne particle;
(e) a processor for determining, using the detected elastic light scatter resulting from the illumination of the single airborne particle, each of the following:
  (i) a size of the single airborne particle; and,
  (ii) a first value for the single airborne particle wherein the first value is one of a depolarization value for the single airborne particle and an intensity differential elastic scattering value for the single airborne particle; and,
(f) the processor further being configured to determine at least one characteristic of the single airborne particle based on the size of the single airborne particle and the first value for the single airborne particle.

20. The single airborne particle optical analyzer of claim 19, wherein:
(a) the single airborne particle has an aerodynamic diameter of no greater than 10 microns.

21. The single airborne particle optical analyzer of claim 19, wherein:
(a) the at least one characteristic identifies the single airborne particle as biological or non-biological.

22. The single airborne particle optical analyzer of claim 19, wherein:
(a) the at least one characteristic identifies the single airborne particle as a specific type of biological particle.

23. The single airborne particle optical analyzer of claim 19, wherein:
(a) said means for illuminating includes a laser, a quarter wave retarder and a birefringent crystal, wherein the quarter water retarder circularly polarizes a beam generated by said laser and wherein said birefringent crystal produces vertically and horizontally polarized beams separated in space by a predetermined distance and said birefringent crystal is disposed relative to said optical sensing zone such that the single airborne particle is illuminated by the vertically and horizontally polarized beams as the single airborne particle passes through the optical sensing zone.

24. The single airborne particle optical analyzer of claim 23, further including:
(a) a horizontal polarization filter being disposed relative to the optical sensing zone and the light detector such that elastic light scatter resulting from the illumination of the single airborne particle by the vertically and horizontally polarized beams passes through said horizontal polarization filter prior to the elastic light scatter being detected by the light detector.

25. A method of detecting and classifying single airborne particles, said method comprising:
(a) directing an airborne sample having a plurality of airborne particles into an optical sensing zone of an optical detector, the airborne sample being taken from an environment surrounding the optical detector;
(b) illuminating a single airborne particle in the optical sensing zone with a first polarized light beam;
(c) determining from the illumination of the single airborne particle with the first polarized light beam, each of the following:
  (i) particle auto-fluorescence; and,
  (ii) a first value for the single airborne particle wherein the first value is a depolarization value for the single airborne particle; and,
(d) determining at least one characteristic of the single airborne particle based on particle auto-fluorescence and the first value for the single airborne particle.

* * * * *